United States Patent [19]
Barak

[11] Patent Number: 6,106,249
[45] Date of Patent: Aug. 22, 2000

[54] PERISTALTIC PUMP

[75] Inventor: Swi Barak, Caesarea, Israel

[73] Assignee: Nestec S.A., Vevey, Switzerland

[21] Appl. No.: 09/030,988

[22] Filed: Feb. 26, 1998

[30] Foreign Application Priority Data

Apr. 18, 1997 [IL] Israel ........................................ 120697
Aug. 7, 1997 [EP] European Pat. Off. .............. 97202451

[51] Int. Cl.[7] .............................. F04B 43/08; F03B 13/00
[52] U.S. Cl. ............................................ 417/474; 419/900
[58] Field of Search ................................... 417/477.4, 18, 417/465, 466, 474, 471; 128/DIG. 12

[56] References Cited

U.S. PATENT DOCUMENTS

| | | | |
|---|---|---|---|
| 3,083,647 | 4/1963 | Miller | 103/148 |
| 3,726,613 | 4/1973 | von Casimir . | |
| 4,586,882 | 5/1986 | Tseng | 417/477 |
| 4,653,987 | 3/1987 | Tsuji et al. | 417/360 |
| 4,781,548 | 11/1988 | Alderson et al. | 417/474 |
| 4,836,752 | 6/1989 | Burkett | 417/12 |
| 4,867,744 | 9/1989 | Borsanyi | 604/153 |
| 4,869,646 | 9/1989 | Gordon et al. . | |
| 5,088,904 | 2/1992 | Okada | 417/474 |
| 5,304,127 | 4/1994 | Kawahara et al. | 604/65 |
| 5,601,420 | 2/1997 | Warner et al. | 417/474 |
| 5,741,121 | 4/1998 | O'Leary | 417/53 |
| 5,888,052 | 3/1999 | Hill | 417/53 |
| 5,924,852 | 7/1999 | Moubayed et al. | 417/474 |

FOREIGN PATENT DOCUMENTS

| | | |
|---|---|---|
| 0 214 443 | 3/1987 | European Pat. Off. . |
| 0 526 962 | 2/1993 | European Pat. Off. . |
| 2 071 222 | 9/1981 | United Kingdom . |

*Primary Examiner*—Teresa Walberg
*Assistant Examiner*—Daniel Robinson
*Attorney, Agent, or Firm*—Hill & Simpson

[57] ABSTRACT

A peristaltic pump for propelling liquid through a flexible tube segment. The pump has a cam shaft which carries a plurality of cams each having a driving surface. The driving surfaces of adjacent cams are spaced at an angle to each other about the cam shaft. The pump also has a plurality of cam followers which are each reciprocal in a common direction perpendicular to the axis of the cam shaft. Each cam follower has a cam surface riding on the driving surface of a cam and a tube engaging surface for engaging the flexible tube segment. At least one of the cam followers is a restriction cam follower of which the tube engaging surface engages the flexible tube segment for a longer period than that of the other cam followers. The pump also has a motor for rotating the cam shaft whereby the cams cause the cam followers to each engage and occlude the flexible tube segment to form a propagating depression wave in the flexible tube segment for propelling liquid. The restriction cam followers prevent back flow of the liquid.

20 Claims, 7 Drawing Sheets

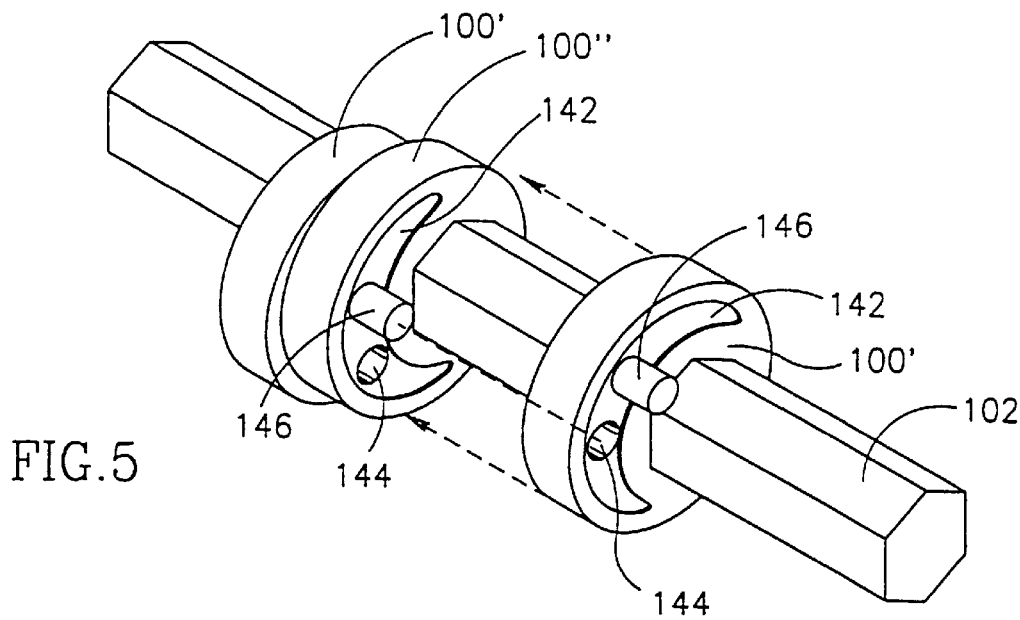
FIG.5
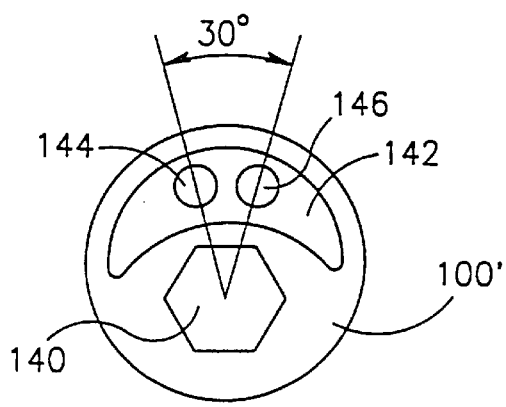
FIG.6A
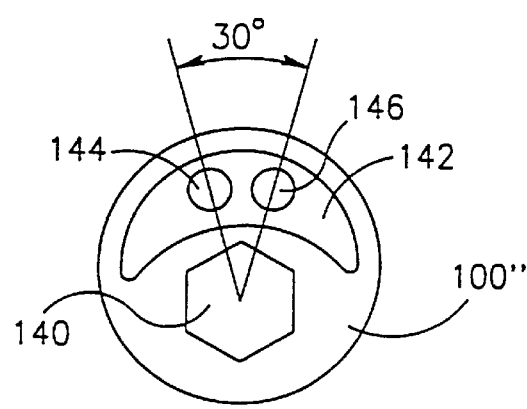
FIG.6B
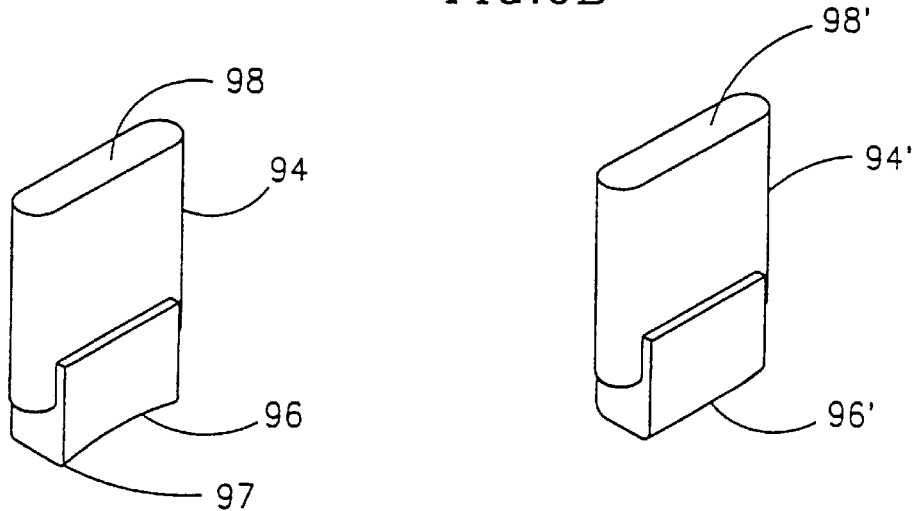
FIG.7A
FIG.7B

PERISTALTIC PUMP

FIELD OF THE INVENTION

This invention relates to a peristaltic pump which is suitable for use in systems for administration of liquids to a patient.

BACKGROUND OF THE INVENTION

Systems for administration of liquids to a patient are widely known. The manner of propelling the liquid to the patient may be by gravitation, by means of pressure applied on a deformable container, or by means of a pump. In pump-operated administration systems, the pump must be capable of administering the liquid in a controlled, continuous manner. A particular example of a pump used in pump-operated administration systems is a peristaltic pump. However, peristaltic pumps are subject to back flow problems.

Therefore there is a need for a peristaltic pump which is able to administer the liquid in a controlled, continuous manner without back flow of liquid.

SUMMARY OF THE INVENTION

This invention provides a peristaltic pump for propelling liquid through a flexible tube segment, the pump comprising:

a cam shaft carrying a plurality of cams each having a driving surface, the driving surfaces of adjacent cams being spaced at an angle to each other about the cam shaft;

a plurality of cam followers which are each reciprocal in a common direction perpendicular to the axis of the cam shaft, each cam follower having a cam surface riding on the driving surface of a cam and a tube engaging surface for engaging the flexible tube segment, at least one of the cam followers being a restriction cam follower of which the tube engaging surface engages the flexible tube segment for a longer period than that of the other cams; and a motor for rotating the cam shaft whereby the cams cause the cam followers to each engage and occlude the flexible tube segment to form a propagating depression wave in the flexible tube segment for propelling liquid; the restriction cam followers preventing back flow of the liquid.

Preferably the tube engaging surfaces of the restriction cam followers extend further from the cams than the tube engaging surfaces of the other cam followers. This may be provided by providing the tube engaging surface of each restriction cam follower with a planar tube engaging surface while the other cam followers have a concave tube engaging surface.

A restriction cam follower is preferably mounted as the terminal cam follower; especially as the terminal cam follower in forward pumping direction of the pump.

The restriction cam follower preferably retracts to open the flexible tube segment only when the rear terminal cam follower is fully extended.

Preferably the pump further comprises sensor means for determining the direction and speed of rotation of the cam shaft. The sensor means may comprise a disc which rotates in accordance with the cam shaft, the disc having a plurality of substantially identical apertures through it equally spaced about its axis; and a pair of sensors mounted adjacent the disc in alignment with the apertures, the sensors being able to determine whether both sensors are aligned in with the same aperture, one sensor is aligned with an aperture but the other is not; and both sensors are not aligned with an aperture, the direction and speed of rotation of the disc being computable from this information.

Each cam is preferably aligned at an angle of 30° with respect to its adjacent cams. Twelve cams may be provided.

The pump may further comprise a housing having a chamber through which the tube segment extends and into which the cam followers reciprocally extend, the chamber having a removable wall element which retains the tube segment between it and the tube engaging surfaces of the cam followers.

The motor preferably may rotate the shaft clockwise and counter-clockwise, enabling liquid to be propelled through the tube segment in both directions.

The cam followers are preferably arranged in a linear array on the shaft and are arranged so that revolution of the cam shaft causes a phase shift in the reciprocation of the cam followers along the linear array. Consequently, the occlusion "advances" in the tube segment from one tube portion to the next, in a continuous wave-like manner. This propels the liquid through the tube segment and hence to the patient through a liquid flow set.

The pump preferably comprises one or more sensors for measurement of flow parameters or parameters of indicative of the pressure within the tube segment. An example of a suitable sensor is a pressure sensor which measures the diameter of the tube segment (which is an indication of the liquid pressure within the tube segment). A particular example of such a pressure sensor is a strain gauge. The determination of the pressure may be important in order to determine existence of flow problems such as, for example, an occlusion in the flow set, and the presence of leaks. Another example of a suitable sensor may be a sensor which tests for existence of air pockets or foam within the tube segment. A particular example of such a sensor is an ultrasonic sensor which measures the attenuation of an ultrasonic signal passing through the tube segment, which is different for liquid or gas. The sensors may be coupled to the control unit for the pump and upon detecting a faulty flow parameter or existence of air pockets or foam, the control unit may be induced to halt the pump, and optionally also to generate an alarm signal.

BRIEF DESCRIPTION OF THE DRAWINGS

Embodiments of the invention are now described, by way of example only, with reference to the drawings in which:

FIG. 5 is an isometric view of a segment of the cam shaft with several cams thereon illustrating the angular diversion between neighboring cams;

FIG. 6A and 6B show axial views of two kinds of cams differing from one another in the angular orientation of the shaft recessing bore;

FIGS. 7A and 7B shows, in isolation, two cam followers, where

FIG. 7A shows a cam follower with a concave tube engaging surface, and

FIG. 7B shows a terminal cam follower with a flat tube engaging surface;

FIG. 8A shows the cam followers in an extended position where they press and occlude a tube segment, and FIG. 8B shows the cam followers in a retracted position disengaged from the tube segment so as to fully open the bore to allow flow of liquid therethrough.

DETAILED DESCRIPTION OF THE PREFERRED EMBODIMENTS

Figure 1:
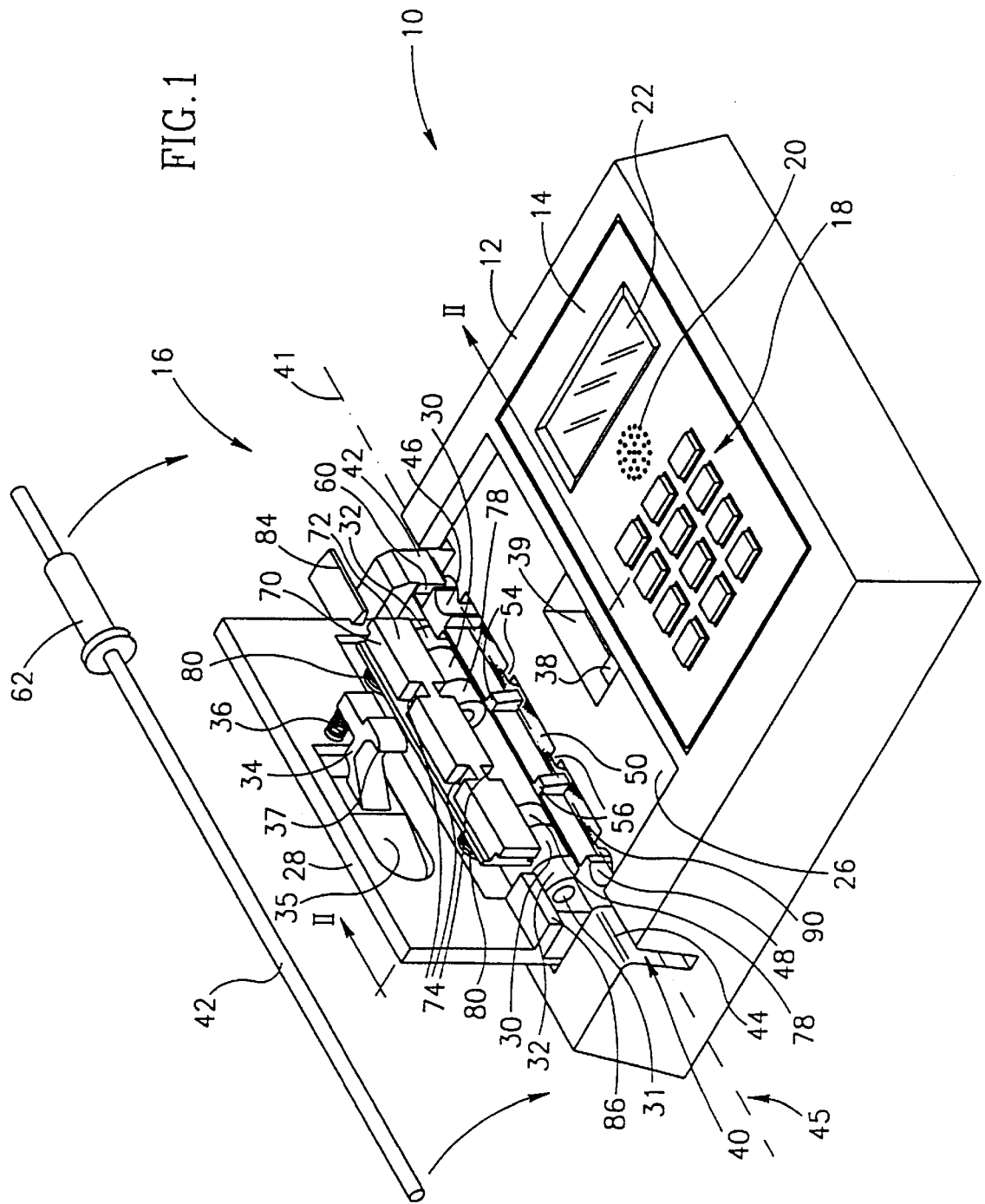
FIG. 1 is a front isometric view of a pump with the receptacle door being open prior to engagement with a tube segment of a flow set.

Referring to the drawings, a pump 10 comprises a housing 12 which has a user interface unit 14 and a pumping assembly 16. The user interface 14 has a key pad 18, an audio signaling element 20, and a display 22. The key pad 18 may be used to initiate or stop the pump and for input of data such as flow rate, flow time, and the like. The audio signaling element 20 is typically a small loudspeaker for providing alarm signals.

The pumping assembly 16 is positioned in a rectangular basin 26 in the housing 12 and includes a motor support structure 33 and a door 28 which closes the opening of the basin 26. The door 28 is hingedly connected to the motor support structure 33 by pivoting members 30, pivots 31 and hinge elements 32. The pivoting members 30 are integral with the door 28 and are connected by the pivots 31 to the hinge elements 32 which are integral with the motor support structure 33. The hinge elements 32 are situated at an end of a projection 32' of the motor support structure 33. The door 28 also includes a latch 34 having a release lever 35, a biasing spring 36 and a hook 37. The hook 37 engages with a lateral shoulder 38 of a locking recess 39 in the housing 12 to lock the door 28 closed on the housing 12.

A channel 40 for receiving a flexible tube segment 42 of a flow set (not shown) extends across the housing 12, between a pair of openings 42 and 44 in the side walls of the housing 12. The channel 40 defines a first axis 45. The channel 40 has a pair of well-shaped portions 46 and 48 at either end which are separated by a primary channel portion 50. The primary channel portion 50 of the channel 40 has two pairs of opposing tube centralizing segments 54 and 56. Adjacent one opening 42, the channel 40 has a cavity 60, which together with the opening 42, serves as a socket for receiving a shaped connector 62 coupled in tube segment 42. The fitting of the shaped connector 62 into the socket ensures correct engagement of the tube segment 42 with the pump 10. Further, the cavity 60 may include a microswitch (not shown) to provide a signal to the control unit of the pump 10 indicative of engagement of the tube segment 42 with the pump 10.

Further the door 32 includes a pair of projections 84 and 86 which, while door 32 is being closed, assist in pushing the tube segment 42 tightly into the channel 40.

A wall element 70 is pivotally coupled to the pivots 31 by pivoting members 78. The wall element 70 has a planar, tube engaging face 72 and has two pairs of recesses 74 in correspondence to centralizing segments 54 and 56. The wall element 70 is coupled to the door 32 by means of biasing springs 80, whereby closing of the door 32 imparts a biasing force on the wall element 70.

Each well-shaped portion 46 and 48 has, at its bottom surface (not shown) a sensor. One of the sensors is an ultrasonic sensor to detect the constituents of the liquid passing through the tube segment 42, in particular to determine whether it contains bubbles or air pockets. The other sensor is a strain gauge for measuring the diameter of the tube segment 42 to determine the pressure of the liquid within the tube segment 42. Any suitable sensors may be used. Suitable sensors are known.

The bottom surface of primary channel portion 50 of the channel 40 is lined with a fabric 90. Therefore, once the tube segment 42 is placed into the channel 40 and the door 32 is closed, the tube segment 42 is retained between the tube engaging face 72 of the wall element 70 and the fabric 90 (see FIG. 2). The fabric 90 may be plastic film or the like. The fabric 90 serves to protect the tube segment 42 against wear and tear.

Figure 2:
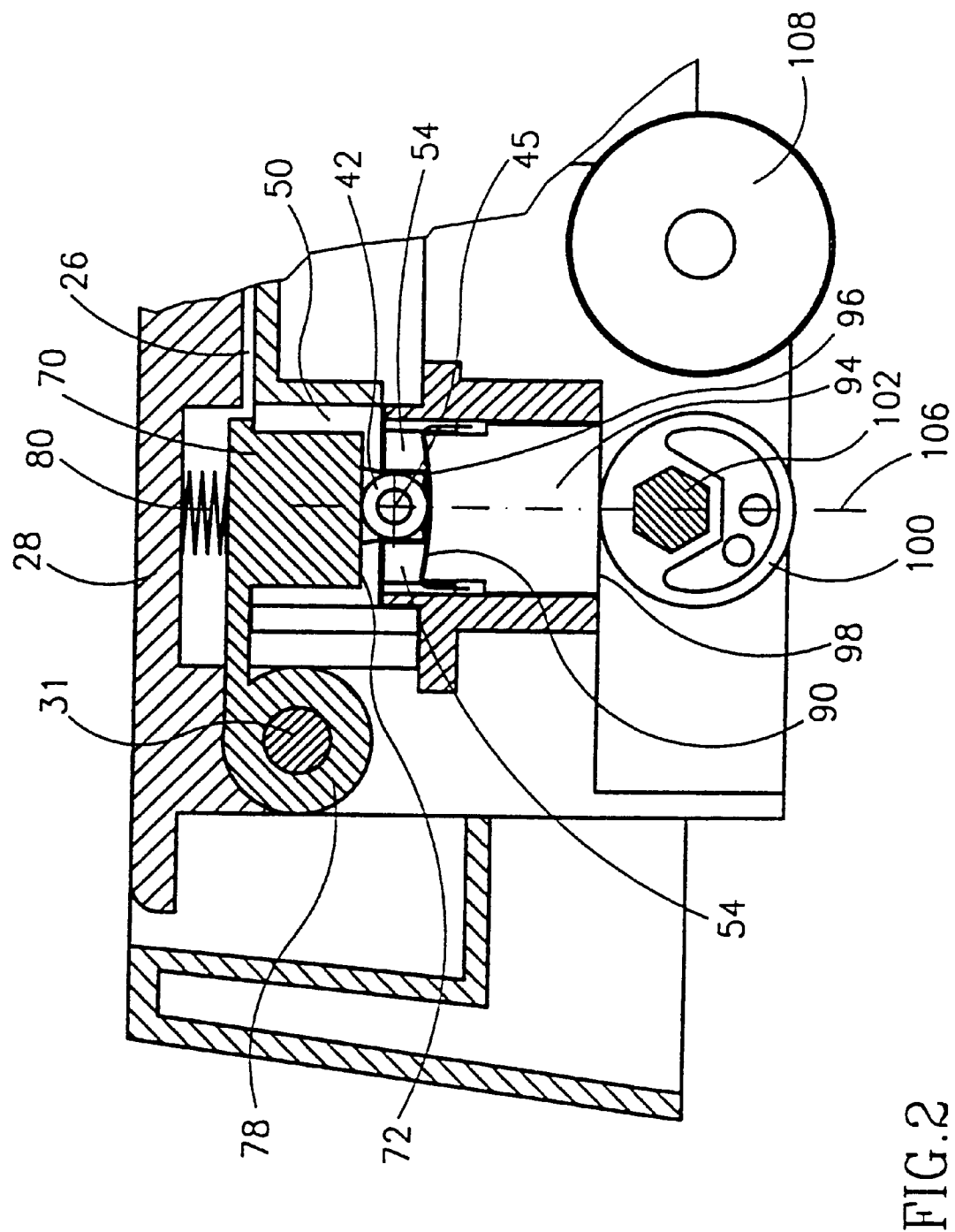
FIG. 2 shows a partial cross-section through lines II—II in FIG. 1, with the door closed and a tube segment in the receptacle.

The pumping mechanism of the pump 10 is formed of a plurality of cams 100 and cam followers 94; the embodiment shown having twelve. As best seen in FIGS. 2 and 7, the cam followers 94 have a tube engaging surface 96 at one end and a cam surface 98 at their opposite end. The cam surface 98 of each cam follower 94 bears on a cam 100. Certain of the cam followers 94 have a concave tube engaging surface 96 which serves to centralize the tube segment 42 within the chamber 40. This prevents distortions in the linear arrangement of the tube segment 42.

Each cam 100 is eccentrically fixed on a hexagonal shaft 102 which lies in an axis parallel to the first axis 45. Due to the eccentric arrangement of the cams 100 on the hexagonal shaft 102, when the cams 100 rotate with the shaft 102, they induce the cam followers 94 to reciprocate linearly in a direction 106 normal to the first axis 45. During this reciprocal movement, the cam followers 94 move between a first, extended position where they depress a portion of tube segment 42 to occlusion, and a second, retracted position (as shown in FIG. 2), where the bore 43 of the tube segment 42 is open to allow liquid flow.

As best illustrated in FIG. 6, each cam 100 has a hexagonal bore 140 into which the hexagonal shaft 102 is received. Further each cam 100 has a crescent-shaped recess 142 in each face. A cylindrical bore 144 extends through each cam 100, from the recess 142 in one face to the recess 142 in the other face. A cylindrical pin 146 projects outwardly from one face of the cam 100 from within the recess 142. The angle between the cylindrical bore 144 and the cylindrical pin 146 on the face, measured from the center of bore 140, is 30°.

The cams 100 are provided in two different configurations. One configuration is illustrated as cam 100' in FIGS. 6A. In this configuration, the crescent-shaped recess 142 is centrally aligned above a side of the hexagonal bore 140. The other configuration is illustrated as cam 100" in FIG. 6B. In this configuration, the crescent-shaped recess 142 is centrally aligned above an apex of the hexagonal bore 142. Hence the two configurations differ from one another in the relative orientation of the hexagonal bore 144 with respect to the remainder of the cam 100, the difference in orientation being 30°.

The cams 100 are mounted on the hexagonal shaft 102 such that a cam 100' of one configuration is followed by a cam 100" of the other configuration. In this way, adjacent cams 100 are aligned at an angle of 30° with respect to one another. When mounted on the hexagonal shaft 102, the cylindrical pin 146 projecting from one cam 100' fits into the cylindrical bore 144 of the adjacent cam 100". In this way, a linear array of cams 100 is obtained, with each cam 100 aligned at an angle of 30° from any adjacent cam 100. The sum of the angles between all twelve cams 100, namely between the first cam 100 in the array and the last one, is 330°. This means that there is a phase difference of 30° in the reciprocation cycle of the cam follower 94 at one end and that at the other end.

Figure 3:
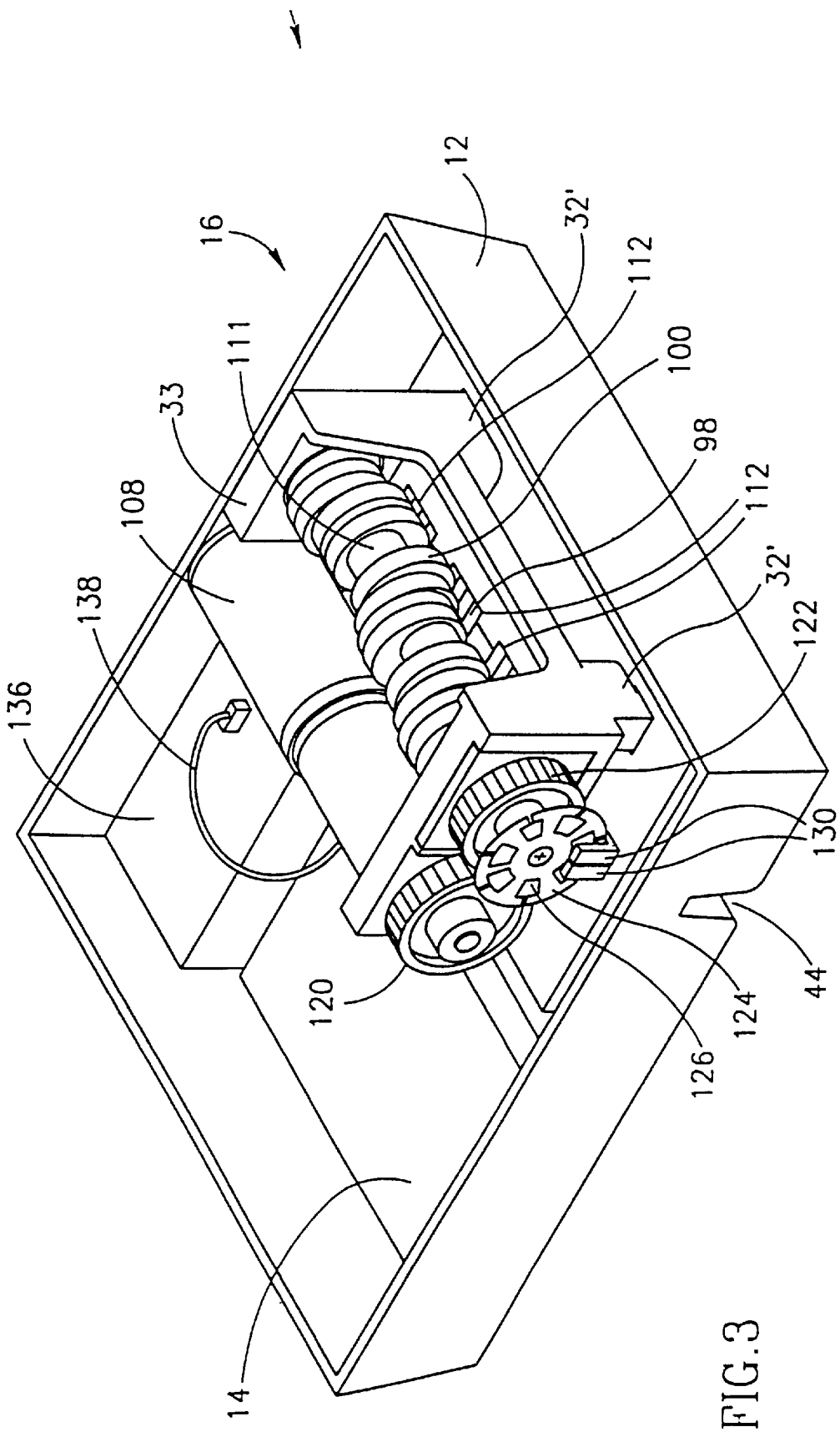
FIG. 3 is a rear isometric view of the pump, with the cover removed to show the internal components.

As can be best seen in FIG. 3, the cam surfaces 98 of the cam followers 94 protrude through openings 112 in the motor support structure 33 towards the cams 100. The cams 100 are arranged in three groups of four cams each, each group corresponding to one of the openings 112. The three groups are separated from one another by spacer elements 111.

Each spacer element 111 has a cylindrical bore at one end for receiving a cylindrical pin 146 projecting from the adjacent cam 100. Also, each spacer element 111 is provided with a cylindrical pin (not shown) at an opposite end for engaging in the cylindrical bore 144 of a cam 100 at that end. A ring (not shown) is mounted at both ends of the array of cams 100 to hold the cams 100 in position on the hexagonal shaft 102. The ring at one end has a cylindrical pin for engaging in the cylindrical bore 144 of the adjacent cam 100 and the ring at the other end has a cylindrical bore for receiving the cylindrical pin 146 of its adjacent cam 100.

One of the cam followers, a restriction cam follower 94', illustrated in FIG. 7B, extends further, in its extended position, towards the tube segment 42 as compared to the other cam followers 94. This may be provided in a number of ways. For example, the restriction cam follower 94' may be slightly longer than the other cam followers 94. Alternatively, if the cam followers 94 have a concave tube engaging surface 96, the restriction cam follower 94' may be provided with a straight or convex tube engaging surface 96'. In the case where the restriction cam follower 94' is provided with a straight tube engaging surface 96', the overall length of the restriction cam follower 94' is the same as that of all the other cam followers 94. If all cam followers 94 were identical, the tube segment 42 at the front cam follower 94 would open prior to complete occlusion of the tube segment 42 at the rear cam follower 94. This would result in a small degree of back flow of fluid in the small time interval prior to complete occlusion of the tube segment 42 at the rear cam follower 94. However, by providing a restriction cam follower 94', this problem may be avoided. Ordinarily the pump 10 has one pumping direction which is defined as the forward pumping direction. The restriction cam follower 94' is preferably positioned as the forward terminal cam follower.

Figure 8A:
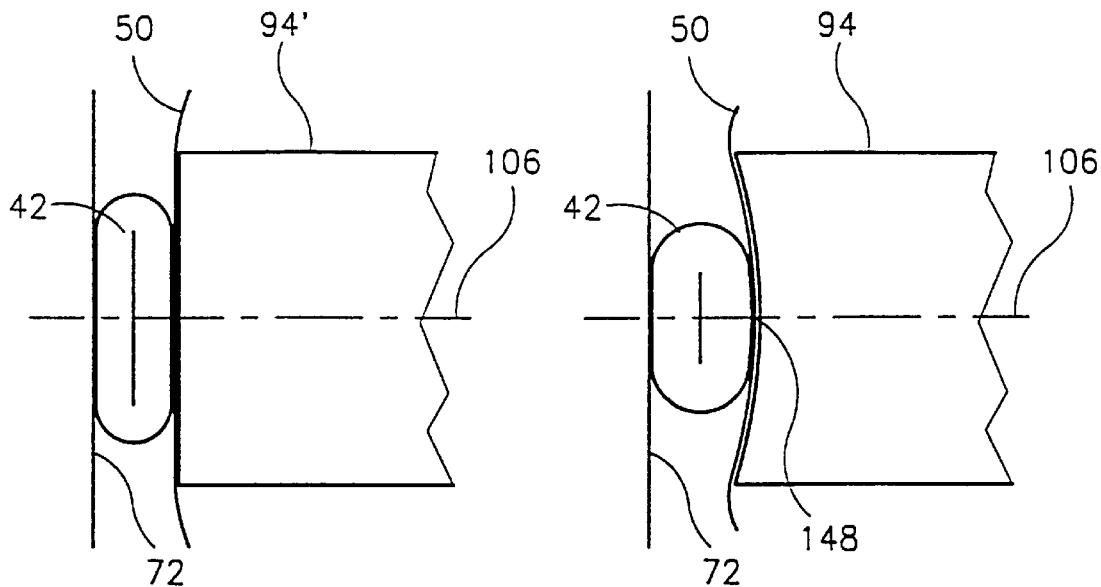
FIGS. 8A and 8B is a schematic representation showing a side view of two different cam followers, both in two operational states, where
Figure 8B:
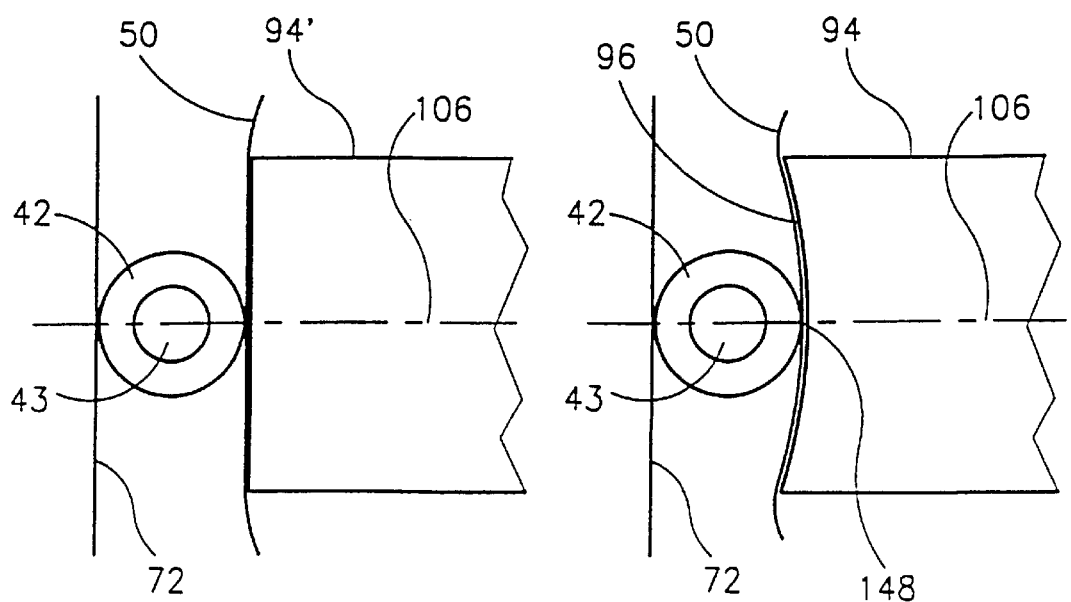

The fully extended and fully retracted position of a standard cam follower 94 and a restriction cam follower 94' are illustrated in FIGS. 8A and 8B. FIG. 8A illustrates both types of cam follower 94 and 94' in their fully extended position in which they occlude a portion of the tube segment 42 through the intermediary of the fabric 90. In the case of the standard cam follower 94, the saddle 148 of the tube engaging surface 96 engages the tube segment 42. Because the restriction cam follower 94' has a planar tube engaging surface 96', the tube engaging surface 96' extends further towards wall 72 and thus squeezes the tube segment 42 to a greater extent as compared to the standard cam follower 94. Both types of cam follower 94 and 94' are illustrated in FIG. 8B in their fully retracted position with the tube segment 42 fully opened to allow flow of liquid through its bore 43.

Figure 4:
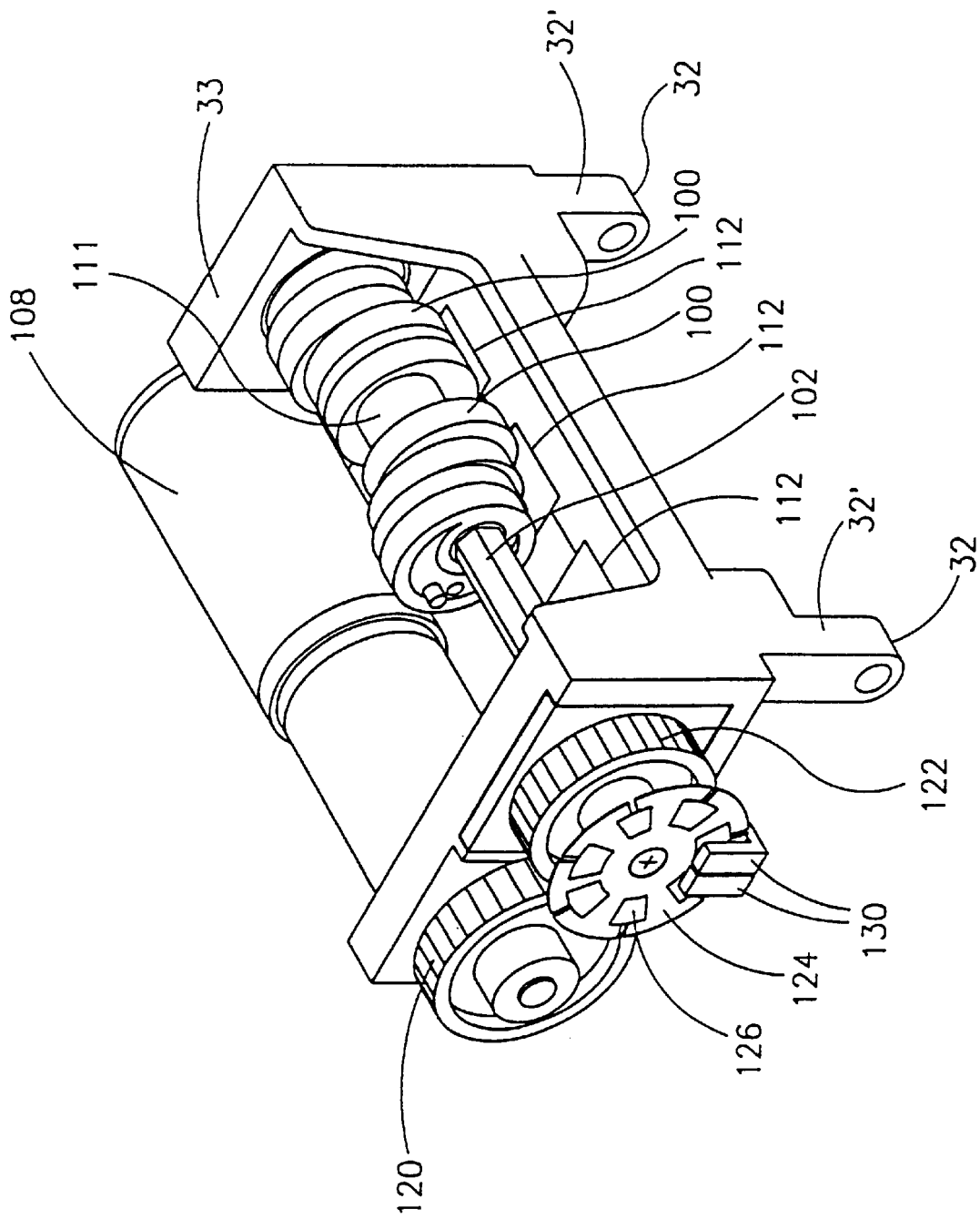
FIG. 4 shows, in isolation, the metal support structure holding the electric motor and the cam shaft, with some of the cams removed, to reveal the shaft.

An electric motor 108 is fixed on the motor support structure. This can best be seen in FIG. 4. The electric motor 108 has a gear wheel 120 coupled to a gear wheel 122 on the hexagonal shaft 102. The motor 108 is connected to a control unit 136 through a cable 138.

An encoder wheel 124 is fixed onto the end of the hexagonal shaft 102. The encoder wheel 124 has a plurality of openings 126 through it and arranged in a circle about the center of the encoder wheel 124. Each opening 126 is of exactly the same size and shape as each other opening 126. Further, each opening 126 is positioned a distance from the center of the encoder wheel 124 equal to that of any other opening 126. Also, the angle between any pair of openings 126 is the same as that between any other pair of openings such that the openings 126 are equi-spaced around the center of the encoder wheel 124. The arc distance between each pair of openings 126 is approximately the same as the arc dimension of each opening 126.

A pair of optical sensors 130 are fixed to the motor support structure 33 in close proximity to the encoder wheel 124 and to each other. The optical sensors 130 are aligned with the openings 126 such that they may determine whether there is an opening 126 in front of them or not. Further, the distance between the optical sensors 130 is such that both sensors may be aligned in front of an opening 126 or in front of the area between a pair of openings 126.

At any point in the rotation of the encoder wheel 124, four possible situations exist. First, both sensors may be in front of an opening 126. Secondly, the first sensor may be in front of an opening 126 while the second is in front of the area between two openings 126. Thirdly, the second sensor may be in front of an opening 126 while the first is in front of the area between two openings 126. Finally, both sensors may be in front of the area between two openings 126. Hence the sensors 130 may be used to monitor the direction and speed of rotation of the openings 126 and hence may be used to determine the direction and speed of rotation of the pump 10. From this, the direction of flow and the flow rate of the liquid through the tube segment 42 may be determined.

The sensors 130 are preferably controlled such that, if one sensor is not working, the other sensor 130 will not function. This prevents miscounting problems which may arise if only one sensor 130 were operating.

Figure 9A:
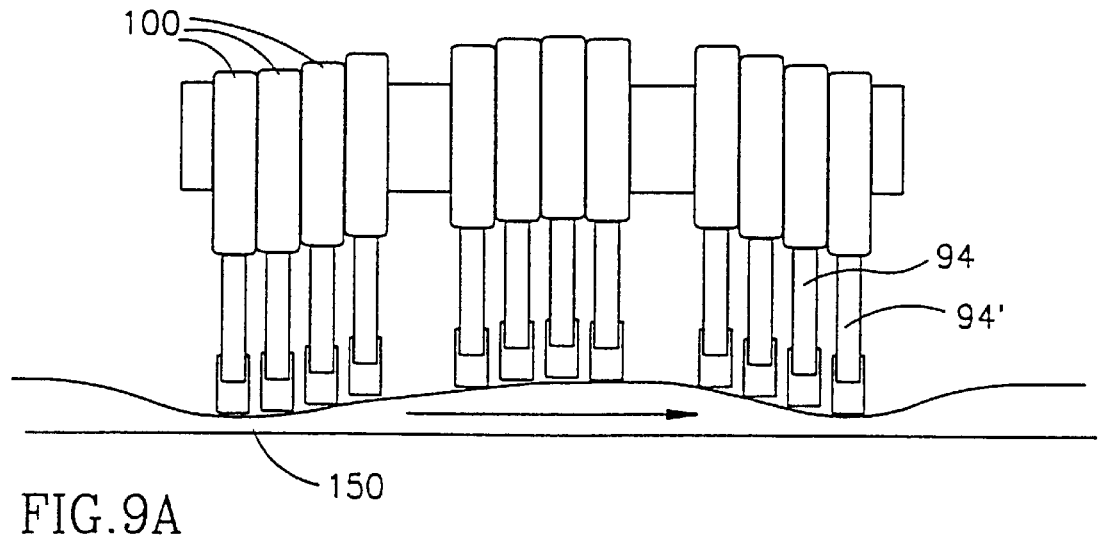
FIG. 9 is a side view showing the cam shaft with the cams mounted thereon, the cam followers and the tube segment, in isolation, in continuous consecutive phases of the pump's operation.
Figure 9B:
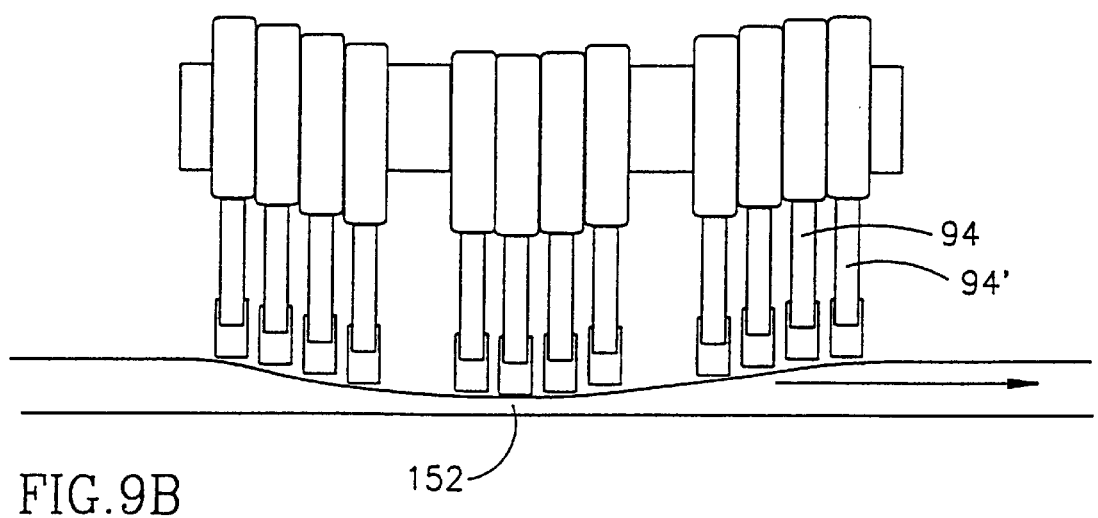
Figure 9C:
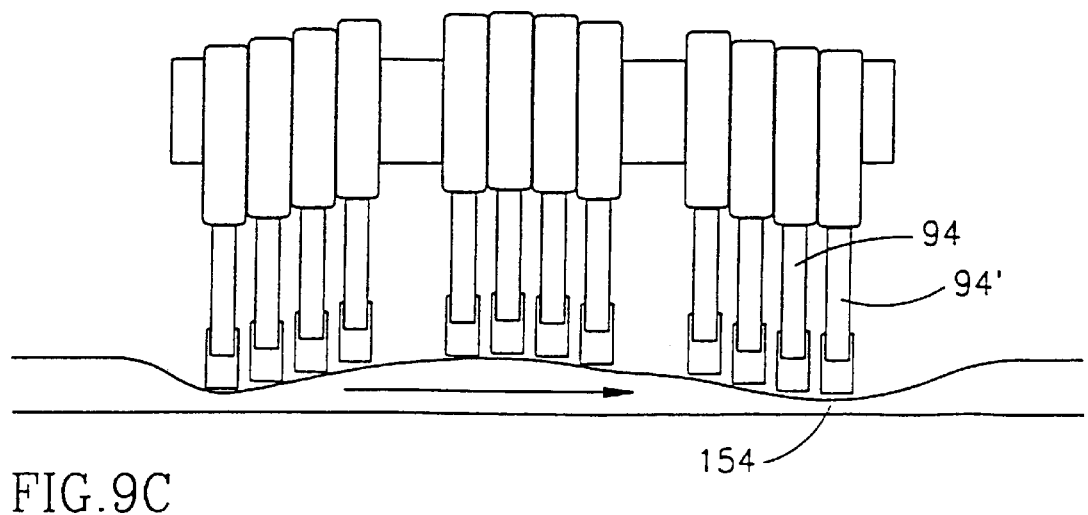

FIG. 9 shows three continuous consecutive phases of the operation of the pump 10. As the cam shaft 102 and the cams 100 turn, the point of occlusion of the tube segment 42 advances from left 150 (FIG. 9A) towards the middle of the segment 152 (FIG. 9B) and to the right 154 (FIG. 9C) in a wave-like fashion. This sequence is repeated continuously and thus a body of liquid is continuously propelled from left to right. The restriction cam follower 94' is typically the right most one. Since it extends further in its extended position, it occludes the tube segment 42 for somewhat longer than the other cam followers 94. This prevents back flow of liquid.

Numerous modifications may be made to the embodiments described above without departing from the scope of the invention. For example, it is not necessary to use twelve cams 100; any suitable number of cams 100 may be used. Also, it is not necessary to use a hexagonal shaft 102. Instead a shaft of any suitable cross-section may be used. For example, if a shaft 102 of octagonal cross-section is used, adjacent cams 100 will be aligned at an angle of about 22.5° with respect to each other. In this case, the total number of cam 100 will conveniently be 16. Further, the cams 100 need not be mounted on the shaft 102 in groups of 4.

Further, the embodiment described causes a single propagating depression in the tube segment. However, this is not essential and the cams 100 may be arranged to cause the depression wave to have more than one cycle.

I claim:

1. A peristaltic pump for propelling liquid through a flexible tube segment, the pump comprising:

a cam shaft carrying a plurality of cams each having a driving surface, the driving surfaces of adjacent cams being spaced at an angle to each other about the cam shaft;

a plurality of cam followers which are each reciprocal in a common direction perpendicular to the axis of the cam shaft, each cam follower having a cam surface riding on the driving surface of a cam and a tube engaging surface for engaging the flexible tube segment, at least one of the cam followers being a restriction cam follower of which the tube engaging surface engages the flexible tube segment for a longer period than that of the other cam followers; and a motor for rotating the cam shaft whereby the cams cause the cam followers to each engage and occlude the flexible tube segment to form a propagating depression wave in the flexible tube segment for propelling liquid; the restriction cam followers preventing back flow of the liquid.

2. A pump according to claim 1 in which the tube engaging surfaces of the restriction cam followers extend further from the cams than the tube engaging surfaces of the other cam followers.

3. A pump according to claim 2 in which the tube engaging surfaces of the restriction cam followers have a planar tube engaging surface while the other cam followers have a concave tube engaging surface.

4. A pump according to claim 1 in which a restriction cam follower is mounted as a terminal cam follower.

5. A pump according to claim 4 in which the restriction cam follower is mounted as the terminal cam follower in a forward pumping direction of the pump.

6. A pump according to claim 5 in which the terminal cam follower retracts to open the flexible tube segment only when a rear terminal cam follower is fully extended.

7. A pump according to claim 1 further comprising sensor means for determining the direction and speed of rotation of the cam shaft.

8. A pump according to claim 7 in which the sensor means comprises:

a disc which rotates in accordance with the cam shaft, the disc having a plurality of substantially identical apertures through it equally spaced about its axis; and a pair of sensors mounted adjacent the disc in alignment with the apertures, the sensors being able to determine at any point in time whether both sensors are aligned with the same aperture, one sensor is aligned with an aperture but the other is not; or both sensors are not aligned with an aperture, monitoring of the changes in alignment of the sensors with the apertures enabling the direction and speed of rotation of the disc to be computed.

9. A pump according to claim 1 in which each cam is aligned at an angle of 30° with respect to its adjacent cams.

10. A pump according to claim 1 further comprising a housing having a chamber through which the tube segment extends and into which the cam followers reciprocally extend, the chamber having a removable wall element which retains the tube segment between it and the tube engaging surfaces of the cam followers.

11. A peristaltic pump for propelling liquid through a flexible tube segment, the pump comprising:

a cam shaft carrying a plurality of cams each having a driving surface, the driving surfaces of adjacent cams being spaced at an angle to each other about the cam shaft;

a plurality of cam followers which are each reciprocal in a common direction perpendicular to the axis of the cam shaft, each cam follower having a cam surface riding on the driving surface of a cam and a tube engaging surface for engaging the flexible tube segment, at least one of the cam followers being a restriction cam follower of which the tube engaging surface extends further from the cams than the tube engaging surfaces of the other cam followers for engaging the flexible tube segment for a longer period than that of the other cam followers; and a motor for rotating the cam shaft whereby the cams cause the cam followers to each engage and occlude the flexible tube segment to form a propagating depression wave in the flexible tube segment for propelling liquid; the restriction cam followers preventing back flow of the liquid.

12. A pump according to claim 11 further comprising sensor means for determining the direction and speed of rotation of the cam shaft.

13. A pump according to claim 12 in which the sensor means comprises:

a disc which rotates in accordance with the cam shaft, the disc having a plurality of substantially identical apertures through it equally spaced about its axis; and a pair of sensors mounted adjacent the disc in alignment with the apertures, the sensors being able to determine at any point in time whether both sensors are aligned with the same aperture, one sensor is aligned with an aperture but the other is not; or both sensors are not aligned with an aperture; monitoring of the changes in alignment of the sensors with the apertures enabling the direction and speed of rotation of the disc to be computed.

14. A pump according to claim 11 in which a restriction cam follower is mounted as a terminal cam follower.

15. A pump according to claim 14 in which the restriction cam follower is mounted as the terminal cam follower in a forward pumping direction of the pump.

16. A peristaltic pump for propelling liquid through a flexible tube segment, the pump comprising:

a cam shaft carrying a plurality of cams each having a driving surface, the driving surfaces of adjacent cams being spaced at an angle to each other about the cam shaft;

a plurality of cam followers which are each reciprocal in a common direction perpendicular to the axis of the cam shaft, each cam follower having a cam surface riding on the driving surface of a can and a tube engaging surface for engaging the flexible tube segment, at least one of the cam followers being a restriction cam follower of which the tube engaging surface engages the flexible tube segment for a longer period than that of the other cam followers;

sensor means for determining the direction and speed of rotation of the cam shaft; and a motor for rotating the cam shaft whereby the cams cause the cam followers to each engage and occlude the flexible tube segment to form a propagating depression wave in the flexible tube segment for propelling liquid; the restriction cam followers preventing back flow of the liquid.

17. A pump according to claim 16 in which the sensor means comprises:

a disc which rotates in accordance with the cam shaft, the disc having a plurality of substantially identical apertures through it equally spaced about its axis; and a pair of sensors mounted adjacent the disc in alignment with the apertures, the sensors being able to determine at any point in time whether both sensors are aligned with the same aperture, one sensor is aligned with an aperture but the other is not; or both sensors are not aligned with an aperture, monitoring of the changes in alignment of the sensors with the apertures enabling the direction and speed of rotation of the disc to be computed.

18. A pump according to claim 16 in which the tube engaging surfaces of the restriction cam followers extend further from the cams than the tube engaging surfaces of the other cam followers.

19. A pump according to claim 16 in which a restriction cam follower is mounted as a terminal cam follower.

20. A pump according to claim 19 in which the restriction cam follower is mounted as the terminal cam follower in a forward pumping direction of the pump.

* * * * *